(12) United States Patent
Ohishi

(10) Patent No.: US 9,913,623 B2
(45) Date of Patent: Mar. 13, 2018

(54) EXPOSURE DOSE MANAGEMENT SYSTEM

(71) Applicant: Toshiba Medical Systems Corporation, Otawara-shi (JP)

(72) Inventor: Satoru Ohishi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 152 days.

(21) Appl. No.: 14/670,559

(22) Filed: Mar. 27, 2015

(65) Prior Publication Data
US 2015/0196267 A1    Jul. 16, 2015

Related U.S. Application Data

(63) Continuation of application No. PCT/JP2013/080905, filed on Nov. 15, 2013.

(30) Foreign Application Priority Data

Nov. 15, 2012  (JP) ................ 2012-251030

(51) Int. Cl.
G01D 18/00   (2006.01)
A61B 6/00    (2006.01)
(Continued)

(52) U.S. Cl.
CPC ............ *A61B 6/542* (2013.01); *A61B 6/4417* (2013.01); *A61B 6/4441* (2013.01);
(Continued)

(58) Field of Classification Search
CPC ..... A61B 6/032; A61B 6/4417; A61B 6/4441; A61B 6/4464; A61B 6/504; A61B 6/5229;
(Continued)

(56) References Cited

U.S. PATENT DOCUMENTS

2004/0146141 A1*  7/2004  Svatos ............... A61N 5/103
                                                    378/65
2007/0127845 A1*  6/2007  Fu .................... A61B 6/4458
                                                    382/294

FOREIGN PATENT DOCUMENTS

JP     2005-124895 A      5/2005
JP     2005124895 A   *  5/2005
(Continued)

OTHER PUBLICATIONS

International Search Report dated Feb. 10, 2014 for PCT/JP2013/080905 Filed on Nov. 15, 2013 (English Language).
(Continued)

*Primary Examiner* — Irakli Kiknadze
(74) *Attorney, Agent, or Firm* — Oblon, McClelland, Maier & Neustadt, L.L.P.

(57) ABSTRACT

An exposure dose management system according to an embodiment includes an image storage device, a first recording device, a misalignment correction device, and a second recording device. The image storage device stores a human body three-dimensional image. The first recording device records an exposure dose and an exposure area of a subject in a first irradiation step on the human body three-dimensional image. The misalignment correction device corrects misalignment between a position of the subject in a second irradiation step, which follows the first irradiation step, and a position of the human body three-dimensional image. The second recording device further records an exposure dose and an exposure area in the second irradiation step on the human body three-dimensional image in which the misalignment was corrected.

13 Claims, 14 Drawing Sheets

(51) Int. Cl.
*A61N 5/10* (2006.01)
*G06F 19/00* (2018.01)
*A61B 6/03* (2006.01)

(52) U.S. Cl.
CPC ............ *A61B 6/4464* (2013.01); *A61B 6/504* (2013.01); *A61B 6/545* (2013.01); *A61B 6/56* (2013.01); *A61B 6/584* (2013.01); *A61N 5/1049* (2013.01); *G06F 19/3437* (2013.01); *A61B 6/032* (2013.01); *A61B 6/5229* (2013.01); *A61N 5/1069* (2013.01); *A61N 5/1071* (2013.01); *A61N 2005/1054* (2013.01); *G06F 19/321* (2013.01); *G06F 19/3481* (2013.01)

(58) Field of Classification Search
CPC ............ A61B 6/542; A61B 6/545; A61B 6/56; A61B 6/584; A61B 6/482; A61B 6/4035; A61B 6/466; A61B 6/4241; A61B 6/4085; A61B 6/583; A61B 6/4014; A61B 6/4291; A61B 6/5205; A61B 5/0071; A61B 5/0073; A61B 6/027; A61B 6/4042; A61B 6/00; A61B 6/488; A61B 6/4423; A61B 6/544; A61B 6/4007; A61B 6/463; A61B 6/481; A61B 6/487; A61B 6/5294; A61B 6/566; A61B 6/12; A61B 6/4233; A61B 6/4411; A61B 5/055; A61B 6/08; A61B 6/4458; A61B 6/461; A61B 6/508; A61B 6/541; A61B 6/582; A61B 6/589; A61N 2005/1054; A61N 5/1049; A61N 5/1069; A61N 5/1071; G06F 19/321; G06F 19/3437; G06F 19/3481; G06T 19/006; G06T 2207/10016; G06T 2207/10116; G06T 2207/30004
USPC ....................................... 378/4, 62, 207, 205
See application file for complete search history.

(56) References Cited

FOREIGN PATENT DOCUMENTS

| JP | 2007-175323 | A |   | 7/2007 |
|----|-------------|---|---|--------|
| JP | 2007175323  | A | * | 7/2007 |
| JP | 2010-068978 | A |   | 4/2010 |
| JP | 2012-143275 | A |   | 8/2012 |
| JP | 2012143275  | A | * | 8/2012 |

OTHER PUBLICATIONS

International Written Opinion dated Feb. 10, 2014 for PCT/JP2013/080905 Filed on Nov. 15, 2013.
K. Chugh et al., "A Computer-Graphic Display for Real-Time Operator Feedback during Interventional X-Ray Procedures", Medical Imaging 2004, SPIE, vol. 5367, pp. 464-473, 2004.

\* cited by examiner

M Human body structure model

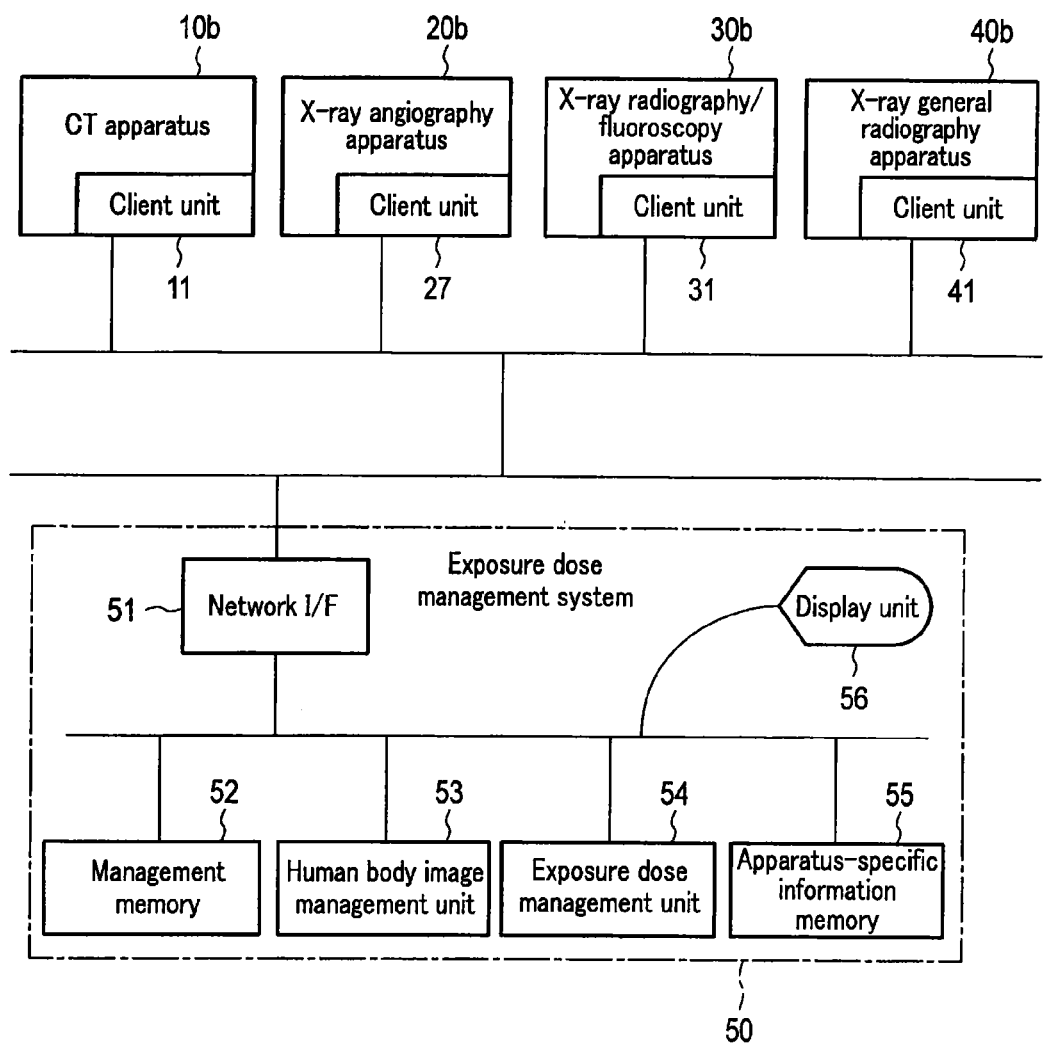
F I G. 13

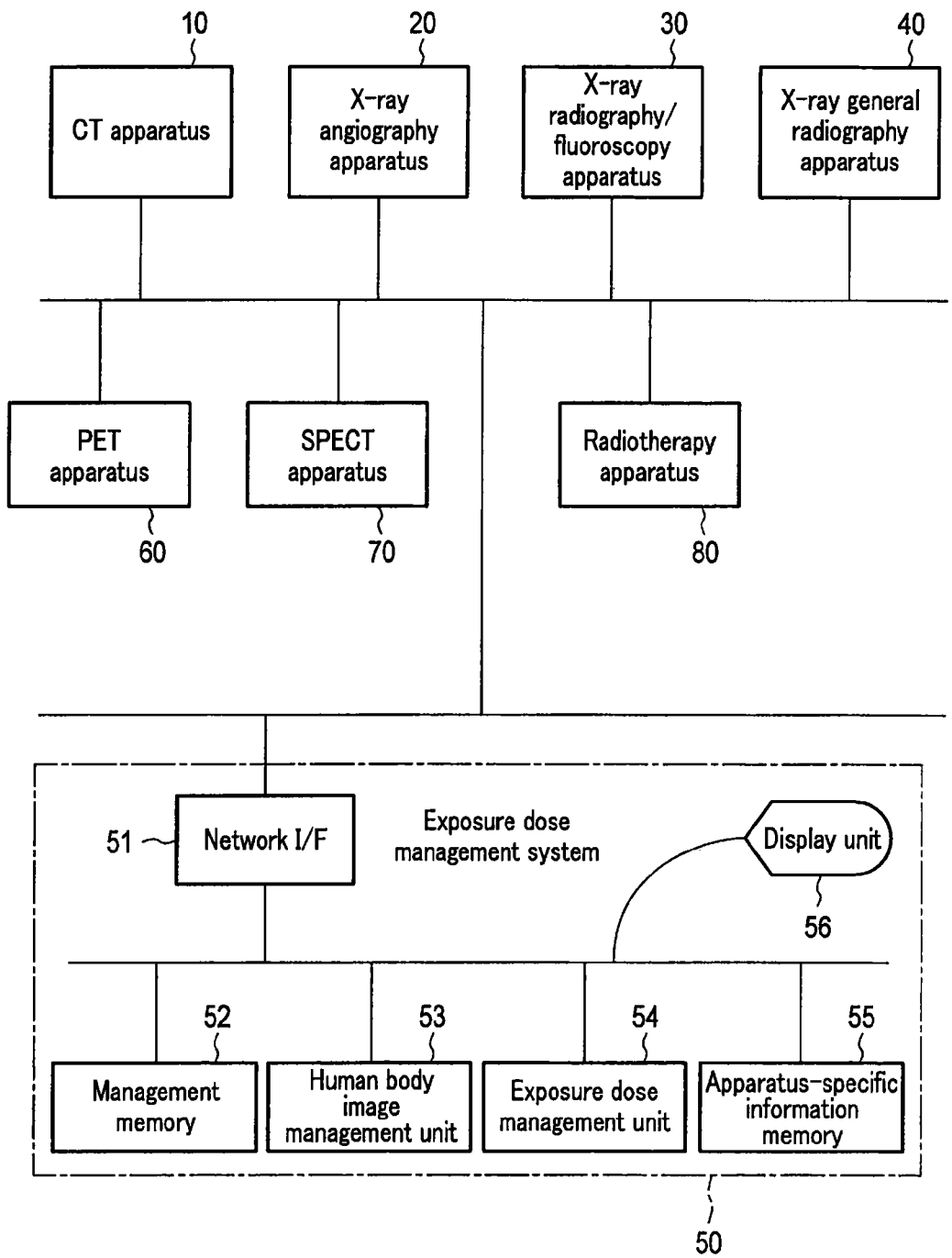
F I G. 15

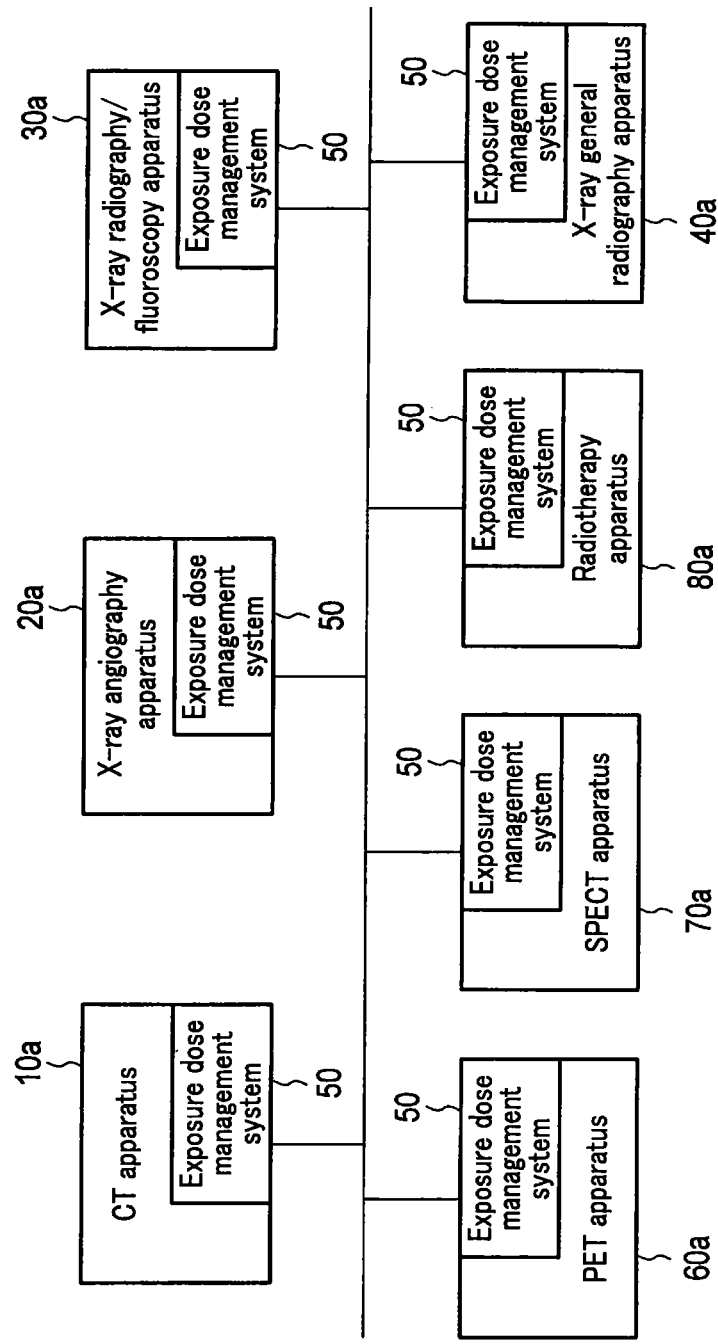
F I G. 16

EXPOSURE DOSE MANAGEMENT SYSTEM

CROSS-REFERENCE TO RELATED APPLICATIONS

This application is a Continuation Application of PCT application No. PCT/JP2013/080905, filed on Nov. 15, 2013, and is based upon and claims the benefit of priority from Japanese Patent Application No. 2012-251030, filed on Nov. 15, 2012; the entire contents of which are incorporated herein by reference.

FIELD

Embodiments described herein relate generally to an exposure dose management system.

BACKGROUND

In order to recognize a patient's disease, an examination involving X-ray irradiation by, for instance, an X-ray diagnosis apparatus and a CT (computed tomography) apparatus, is indispensable. However, while the examination involving X-ray irradiation provides an advantage that it may allow the disease of the patient to be recognized, the examination is also disadvantageous in the respect of exposing the patient to X-rays. Thus, it is important to manage the exposure dose of the patient from the standpoint of minimizing the exposure dose of the patient and understanding the risk of exposure damage.

Incidentally, the IEC (International Electrotechnical Commission) standards require measurement of CTDIw (weighted CT dose index) and DLP (dose-length product) for a CT apparatus, and require measurement of an incidence surface dose for an angiography apparatus.

On the other hand, radiation exposure damage first occurs on the skin. In order to understand the risk of such radiation exposure damage, it is necessary to manage the total dose of radiation exposure on the skin (skin exposure dose).

However, the skin exposure dose cannot be totally managed in one examination by such indices as CTDIw, DLP and incidence surface dose.

Meanwhile, there has been proposed an exposure dose management system in which a skin exposure dose in one examination using the angiography apparatus is integrated and displayed on a human body shape model (surface shape only).

However, in the above-described exposure dose management system, although the skin exposure dose in one examination can be managed, there is room for improvement as described below, according to the inventor's study.

In usual cases, a diagnosis and a medical treatment are not completed by a single examination. For example, a diagnosis and a medical treatment are completed after a plurality of steps, such as a diagnosis by a CT apparatus, a medical treatment by an angiography apparatus and a confirmation of an operation by the CT apparatus. Thus, the exposure dose management in one examination is not sufficient, and an exposure dose management corresponding to a plurality of times of X-ray irradiation becomes necessary.

In addition, it is known that the skin exposure dose recovers based on elapsed time during a plurality of times of X-ray irradiation, but the part that did not recover accumulates in the patient. Thus, if CT examinations are conducted today and tomorrow, the exposure dose accumulated after the examination of tomorrow becomes higher than the exposure dose accumulated after the examination of today.

Therefore, it is necessary to manage the exposure dose accumulated by multiple times of X-ray irradiation.

However, in the conventional exposure dose management system, there is room for improvement in that the exposure dose accumulated by such multiple times of X-ray irradiation cannot be managed. Being able to manage such would be advantageous not only for the management of the skin exposure dose accumulated by X-ray irradiation, but also for the management of the exposure dose of internal organs with high sensitivity to exposure, such as the eye and thyroid gland. Further, the same applies to an exposure dose of an arbitrary region by an arbitrary radiation, such as an internal organ exposure dose accumulated by gamma ray irradiation. Specifically, in the conventional exposure dose management system, there is room for improvement in that the exposure dose accumulated by multiple times of irradiation cannot be managed.

The object is to provide an exposure dose management system which can manage an exposure dose accumulated by multiple times of irradiation.

BRIEF DESCRIPTION OF THE DRAWINGS

FIG. 13 is a schematic view illustrating an example of an exposure dose management system according to a fourth embodiment and a peripheral configuration thereof.

FIG. 15 is a schematic view illustrating an example of an exposure dose management system according to a fifth embodiment and a peripheral configuration thereof.

FIG. 16 is a schematic view illustrating an example of an exposure dose management system according to a sixth embodiment and a peripheral configuration thereof.

DETAILED DESCRIPTION

In general, according to one embodiment, an exposure dose management system includes an image storage device, a first recording device, a misalignment correction device, and a second recording device.

The image storage device stores a human body three-dimensional image.

The first recording device records an exposure dose and an exposure area of a subject in a first irradiation step on the human body three-dimensional image.

The misalignment correction device corrects misalignment between a position of the subject in a second irradiation step, which follows the first irradiation step, and a position of the human body three-dimensional image.

The second recording device further records an exposure dose and an exposure area in the second irradiation step on the human body three-dimensional image in which the misalignment was corrected.

Exposure dose management systems according to embodiments will be described hereinafter with referenced to the accompanying drawings. The exposure dose management systems to be described below can be implemented by either a hardware configuration or a combined configuration of hardware resources and software. As the software of the combined configuration, use is made of a program which is preinstalled in a computer over a network or from a storage medium, and which causes this computer to execute functions of the exposure dose management system. In addition, in first to fourth embodiments, a case of skin exposure by X-rays is mainly described by way of example. However, fifth to seventh embodiments are realizable also in a case of internal organ exposure by gamma rays or exposure by arbitrary radiation, like the first to fourth embodiments. In short, each embodiment is similarly realizable with respect to exposure of an arbitrary region by an arbitrary radiation.

FIRST EMBODIMENT

Figure 1:
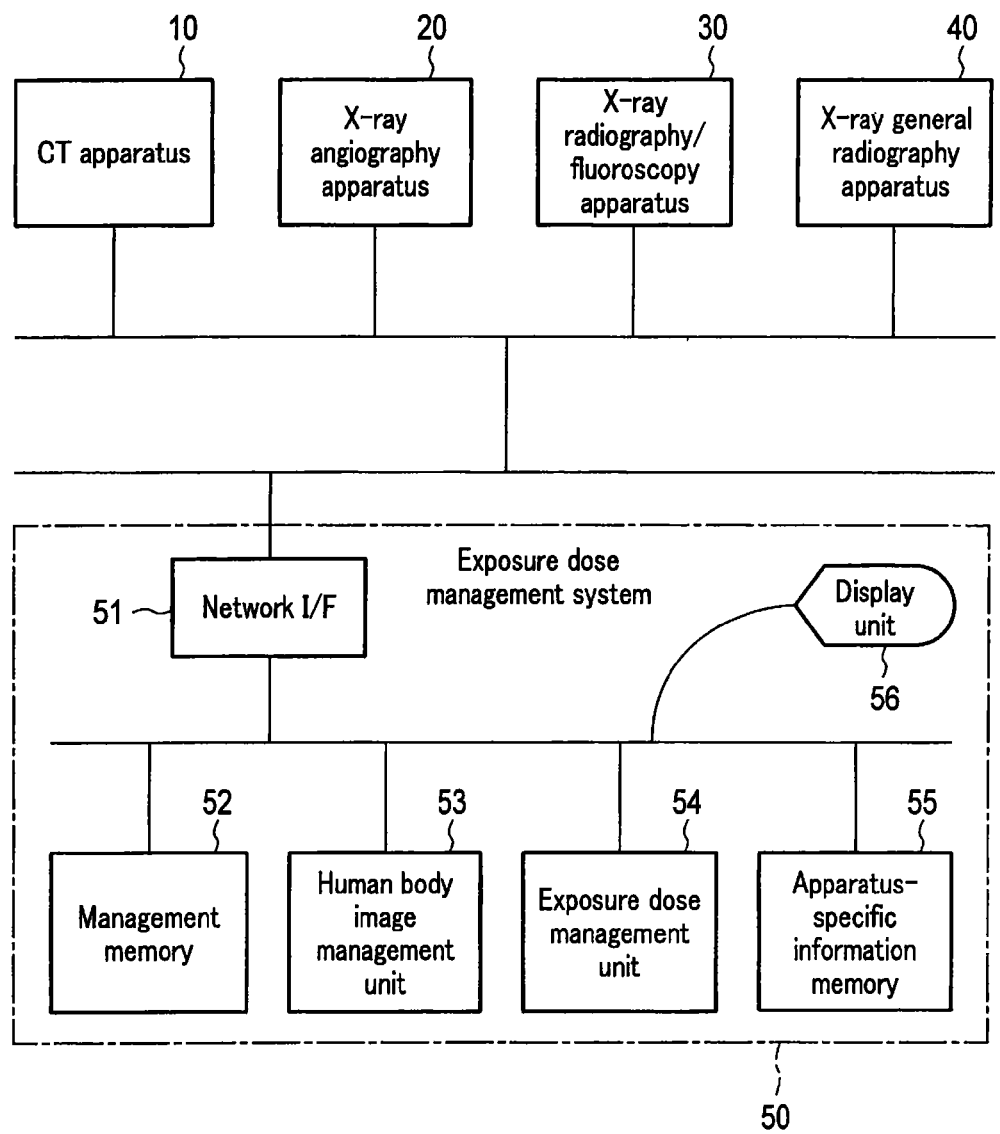
FIG. 1 is a schematic view illustrating an example of an exposure dose management system according to a first embodiment and a peripheral configuration thereof.
Figure 2:
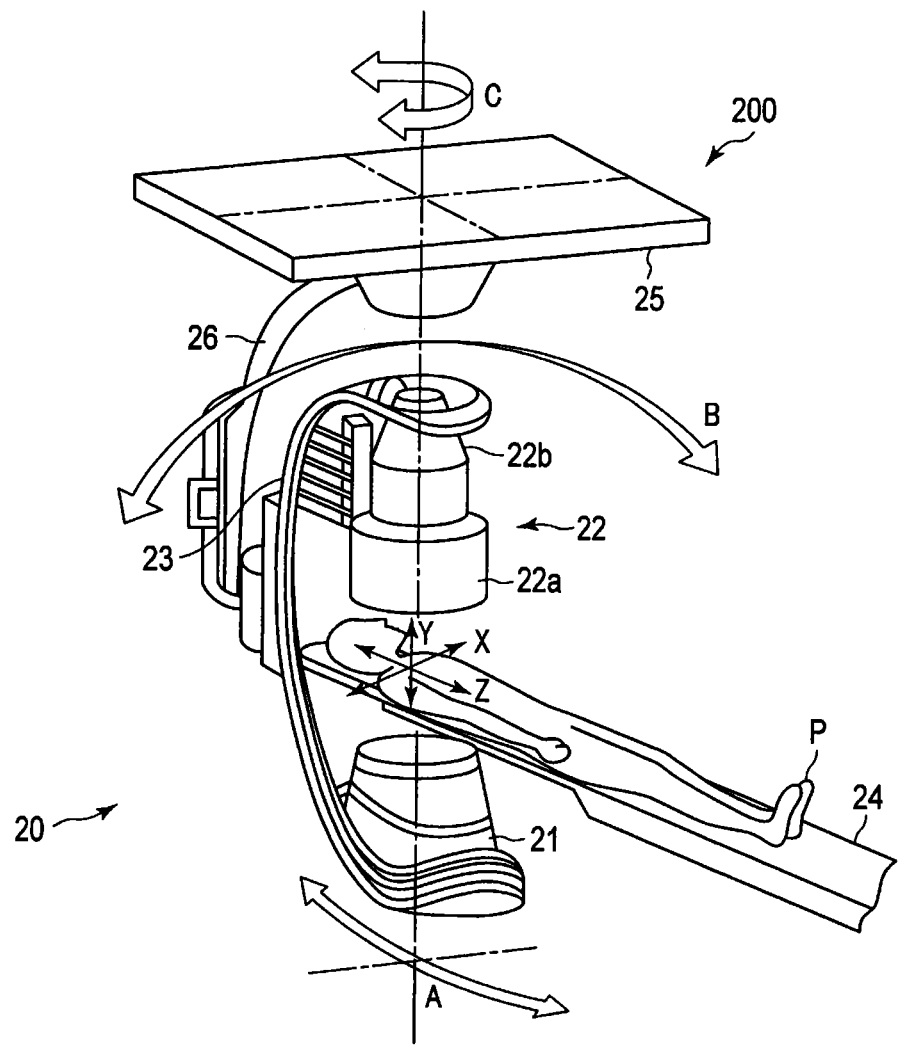
FIG. 2 is a schematic view illustrating a structure of a main part of an X-ray angiography apparatus in the embodiment.

FIG. 1 is a schematic view illustrating an example of an exposure dose management system according to a first embodiment and a peripheral configuration thereof. FIG. 2 is a schematic view illustrating a structure of a main part of an X-ray angiography apparatus 20. As illustrated in FIG. 1, a CT apparatus 10, an X-ray angiography apparatus 20, an X-ray radiography/fluoroscopy (X-ray R/F) apparatus 30 and an X-ray general radiography apparatus 40 are connected to an exposure dose management system 50 over a network.

In this case, the CT apparatus 10 is used for an examination including an X-ray irradiation step, and includes an ordinary CT function. In addition, the CT apparatus 10 includes a function of sending, upon completion of an examination, an X-ray image collected by CT imaging and an X-ray irradiation record corresponding to the X-ray image to the exposure dose management system 50.

Incidentally, since this X-ray image is used for alignment on the exposure dose management system 50 side, it is desirable that the X-ray image be transmitted in a properly reduced size. The transmission with the reduced size is also desirable for the other apparatuses 20, 30 and 40.

The X-ray irradiation record includes geometrical information of an X-ray optical system (an area of a detector where X rays are radiated; a position/angle of the X-ray detector; a position/angle of an X-ray tube; the kind of beam hardening filter before the X-ray tube; etc.) and X-ray conditions. In addition, the X-ray irradiation record includes a subject ID, identification information of an X-ray irradiation step, and date/time information indicative of the date/time of the X-ray irradiation step. The same applies to the X-ray irradiation records of the other apparatuses 20, 30 and 40. In the meantime, for example, in fluoroscopy (X-ray irradiation with a low dose) using the X-ray angiography apparatus 20, there is a case in which an image is not saved. In such a case, only an X-ray irradiation record, without a corresponding image, may be sent. The same applies to the other apparatuses.

The X-ray angiography apparatus 20 is used for an examination or medical treatment including an X-ray irradiation step, and includes a normal angiography function. In addition, the X-ray angiography apparatus 20 includes a function of sending, upon completion of an examination or medical treatment, an X-ray image collected by angiography and an X-ray irradiation record corresponding to the X-ray image to the exposure dose management system 50.

FIG. 2 illustrates a structure of a main part of the X-ray angiography apparatus 20. An X-ray tube 21 generates X rays by application of a high voltage (tube voltage) from a high voltage generator (not shown). The X-ray tube 21 is attached to one end of a C arm 23. An X-ray detector 22 is attached to the other end of the C arm 23 so as to face the X-ray tube 21. For example, as illustrated in FIG. 2, the X-ray detector 22 is composed of an image intensifier 22a and a TV camera 22b, but may be composed of a flat-panel detector which is configured such that a plurality of detection elements (pixels), which directly or indirectly convert incident X rays to an electric charge are arranged two-dimensionally. At a time of imaging, a subject P is disposed between the X-ray tube 21 and X-ray detector 22 in a state in which the subject P is placed on a bed 24.

In a C arm support mechanism 200, the C arm 23 is supported via a suspension arm 26 from a ceiling base 25, such that the C arm 23 is rotatable, with predetermined restrictions, in directions of arrows A, B and C with respect to three XYZ orthogonal axes so as to be able to freely vary the imaging angle relative to the subject P. Incidentally, a straight line extending from an X-ray focus of the X-ray tube 21 through the center of the detection surface of the X-ray detector 22 is referred to as an "imaging axis". Typically, an imaging angle is defined as a crossing angle of the imaging axis to the three XYZ orthogonal axes. Conventionally, the imaging angle is expressed as the angle of each of a right anterior oblique position (RAO), a left anterior oblique position (LAO), a left posterior oblique position (LPO) and a right posterior oblique position (RPO). Typically, the Z axis is defined as an axis substantially agreeing with the body axis of the subject, and the Y axis agreeing with the imaging axis and the X axis intersect with the Z axis at a fixed point of imaging (isocenter).

The X-ray radiography/fluoroscopy apparatus 30 is used for an examination or medical treatment including an X-ray irradiation step, and includes a normal radiography/fluoroscopy function. In addition, the X-ray radiography/fluoroscopy apparatus 30 includes a function of transmitting, upon completion of an examination or medical treatment, an X-ray image collected by X-ray radiography/fluoroscopy and an X-ray irradiation record corresponding to the X-ray image to the exposure dose management system 50.

The X-ray general radiography apparatus 40 is used for an examination including an X-ray irradiation step, and includes a normal X-ray general radiography function. In addition, the X-ray general radiography apparatus 40 includes a function of transmitting, upon completion of an examination or medical treatment, an X-ray image collected by X-ray general radiography and an X-ray irradiation record corresponding to the X-ray image to the exposure dose management system 50.

On the other hand, as illustrated in FIG. 1, the exposure dose management system 50 includes a network I/F 51, a management memory 52, a human body image management unit 53, an exposure dose management unit 54, an apparatus-specific information memory 55, and a display unit 56.

The network I/F 51 includes a function of communicating with the respective apparatuses 10 to 40 via a network. For example, the network I/F 51 includes a function of receiving radiation images (e.g., X-ray images) and irradiation records (e.g., X-ray irradiation records) from the respective apparatuses 10 to 40, and a function of sending the received radiation images and irradiation records to the human body image management unit 53.

The management memory 52 stores human body three-dimensional images and exposure management information. The exposure management information includes human body image management information and exposure dose management information.

Figure 3:
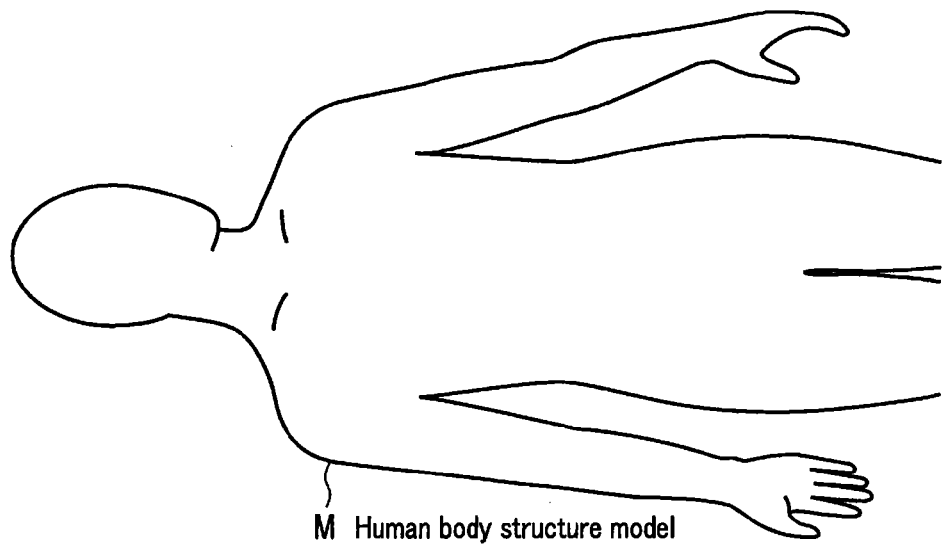
FIG. 3 is a schematic view illustrating a human body structure model in the embodiment.

As the human body three-dimensional image, the data which relates to almost the entire body is stored. As the human body three-dimensional image, use is made of, with respect to each subject, either a CT image of the subject, or a human body structure model M (FIG. 3) which is expressed by a radiation absorption coefficient (e.g., an X-ray absorption coefficient). The human body three-dimensional image of each subject is associated with data of an exposure dose and an exposure area with respect to each irradiation step. As the human body three-dimensional image, a human body three-dimensional image which was created in the past may be reused. In addition, the human body three-dimensional image can be identified by a human body three-dimensional ID. Furthermore, the exposure dose may include a skin exposure dose or an internal organ exposure dose. As the unit of an exposure dose, for example, [μR/min], [μGy] and [mGy] can be used as needed. Further, in the case of a nuclear medicine examination such as PET (positron emission computed tomography), which will be described later, for example, [MBq], which is the unit corresponding to a dose of a radioactive pharmaceutical (RI: radioisotope), may be used as needed as the unit of an exposure dose.

Additionally, it is desirable that the management memory 52 prestore human body structure models M of some body shapes. Additionally, in the present embodiment, human body structure models M having bone structures are stored in advance. Such human body structure models M can be created from, for example, a data bank of CT images. Additionally, use may be made of standard human body three-dimensional images which were created based on data examined by public organizations such as governmental organizations and academic institutes. Additionally, as the method of creation, such a method may typically be used, as needed, in which a phantom made with fineness in minute parts of the internal structure is imaged by volume scan such as helical scan by, e.g., an X-ray CT apparatus, thereby constructing three-dimensional data (also referred to as volume data). From this three-dimensional data, data relating to three-dimensional images of respective regions is extracted by a threshold process or the like. Each region means an internal organ or an organ, such as the eye or generative organ.

The human body image management information is information in which a subject ID, a human body three-dimensional image ID, identification information of an irradiation step, a subject position, a posture and a body shape are associated.

The exposure dose management information is information in which a subject ID, a human body three-dimensional image ID, identification information of an irradiation step, date/time information indicative of the date/time of an irradiation step, a skin exposure dose and a skin exposure area are associated. Incidentally, the identification information or date/time information may be omitted as needed.

The human body image management unit 53 is a functional unit which manages the human body three-dimensional image and human body image management information, and executes a human body image management step ST30 (ST31 to ST36) illustrated in FIG. 5, which will be described later. To give a supplementary description, the human body image management unit 53 includes the following function (f53-1).

(f53-1) A misalignment correction function for correcting misalignment between a position of a subject in a second irradiation step, which follows a first irradiation step, and a position of a human body three-dimensional image.

In the meantime, the misalignment correction function (f53-1) may locally correct misalignment each time a radiation image of the subject is acquired. In addition, the misalignment correction function (f53-1) may end the misalignment correction if the misalignment decreases to a predetermined amount or less.

Additionally, the human body image management unit 53 may include the following functions (f53-2) and (f53-3).

(f53-2) A function of comparing, when the human body three-dimensional image is a human body structure model M, local regions between a radiation image of the subject in each irradiation step and the human body structure model M, and associating these local regions with each other.

(f53-3) A function of distorting the human body structure model M, based on the associated result.

Figure 7:
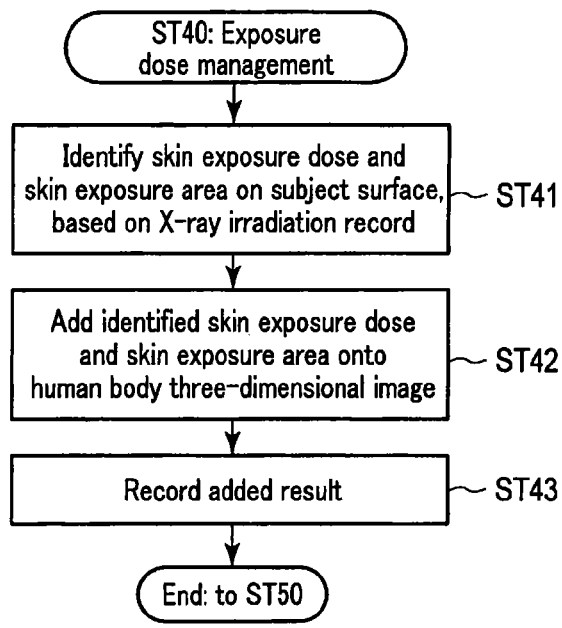
FIG. 7 is a flowchart for describing steps of exposure dose management in the embodiment.

The exposure dose management unit 54 is a functional unit which manages exposure dose management information, and executes an exposure dose management step ST40 (ST41 to ST43) illustrated in FIG. 7 and a display step ST50 (ST51 to ST55) illustrated in FIG. 8, which will be described later. To give a supplementary description, the exposure dose management unit 54 includes the following functions (f54-1) and (f54-2).

(f54-1) A first recording function of recording a skin exposure dose of a subject and a skin exposure area in a first X-ray irradiation step on a human body three-dimensional image.

(f54-2) A second recording function of further recording an exposure dose and an exposure area in a second irradiation step on the human body three-dimensional image in which misalignment was corrected by the human body management unit 53.

Additionally, the exposure dose management unit 54 may include the following functions (f54-3) to (f54-5).

(f54-3) A function of recalculating the exposure dose and exposure area, based on the amount corrected by the human body management unit 53.

(f54-4) A function of reading out, upon accepting an input of a display request designating identification information or time range information indicative of a time range including the date/time, the exposure dose and exposure area from the management memory 52, based on the designated identification information or time range information.

(f54-5) An exposure dose display function of sending to the display unit 56 the image data for displaying the sum of the read-out exposure dose and exposure area on the human body three-dimensional image. Incidentally, the exposure dose management unit 54 and display unit 56 constitute exposure dose display device.

In addition, the exposure dose management unit 54 may include functions (f54-6) to (f54-8), aside from the functions (f54-4) and (f54-5).

(f54-6) A function of of reading out, upon accepting an input of a display request designating identification information or time range information indicative of a time range including the date/time, the exposure dose, exposure area and date/time information from the management memory 52, based on the designated identification information or time range information.

(f54-7) A function of calculating the sum of each of a non-recovered exposure dose and an exposure area, based on the read-out exposure dose and exposure area and a recovery degree which is determined by an elapsed time from the date/time indicated by the read-out date/time information. Incidentally, the recovery degree may have a value varying from region to region.

(f54-8) An exposure dose display function of sending to the display unit 56 the image data for displaying the calculated exposure dose and exposure area on the human body three-dimensional image. Incidentally, the exposure dose management unit 54 and display unit 56 constitute exposure dose display device.

Furthermore, the exposure dose management unit 54 may include a function (f54-9).

(f54-9) An update function of updating, based on the exposure dose and date/time information in the management memory 52, this exposure dose to a zero value, if a predetermined period has passed since the date/time indicated by this date/time information.

The apparatus-specific information memory 55 stores apparatus-specific information which is specific to each apparatus 10, 20, 30, 40. The apparatus-specific information includes, for instance, the shape/material of the beam hardening filter, the material/shape of the bed, and other structures (e.g., a gantry cover of a CT apparatus) existing between the X-ray tube and detector.

The display unit 56 displays processing results, etc. of the respective management units 53 and 54.

Next, the operation of the exposure dose management system with the above-described structure is described with reference to FIG. 4 to FIG. 9. In the present embodiment, the case in which the radiation is X rays and the exposure dose is a skin exposure dose is described by way of example.

Figure 4:
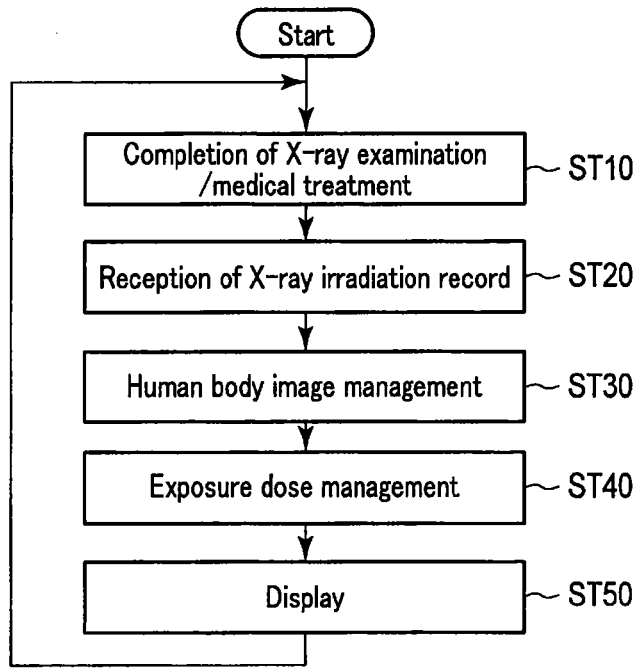
FIG. 4 is a flowchart for describing an operation in the embodiment.

It is now assumed that, as illustrated in FIG. 4, an examination or medical treatment was completed by any one of the CT apparatus 10, X-ray angiography apparatus 20, X-ray radiography/fluoroscopy apparatus 30 and X-ray general radiography apparatus 40. In this case, it is assumed that an examination or medical treatment was completed by the X-ray angiography apparatus 20 (ST10).

The X-ray angiography apparatus 20 sends all X-ray images, which were collected in an X-ray irradiation step included in the examination or medical treatment, and a corresponding X-ray irradiation record to the exposure dose management system 50 via the network I/F 51. In this case, the X-ray irradiation record includes geometrical information of the X-ray optical system, X-ray conditions, subject ID, identification information of an X-ray irradiation step, and date/time information of the X-ray irradiation step.

In the exposure dose management system 50, the network I/F 51 receives the X-ray images and X-ray irradiation record (ST20), and sends X-ray images and X-ray irradiation record to the human body image management unit 53.

The human body image management unit 53 executes human body image management, based on the X-ray image and X-ray irradiation record (ST30).

Figure 5:
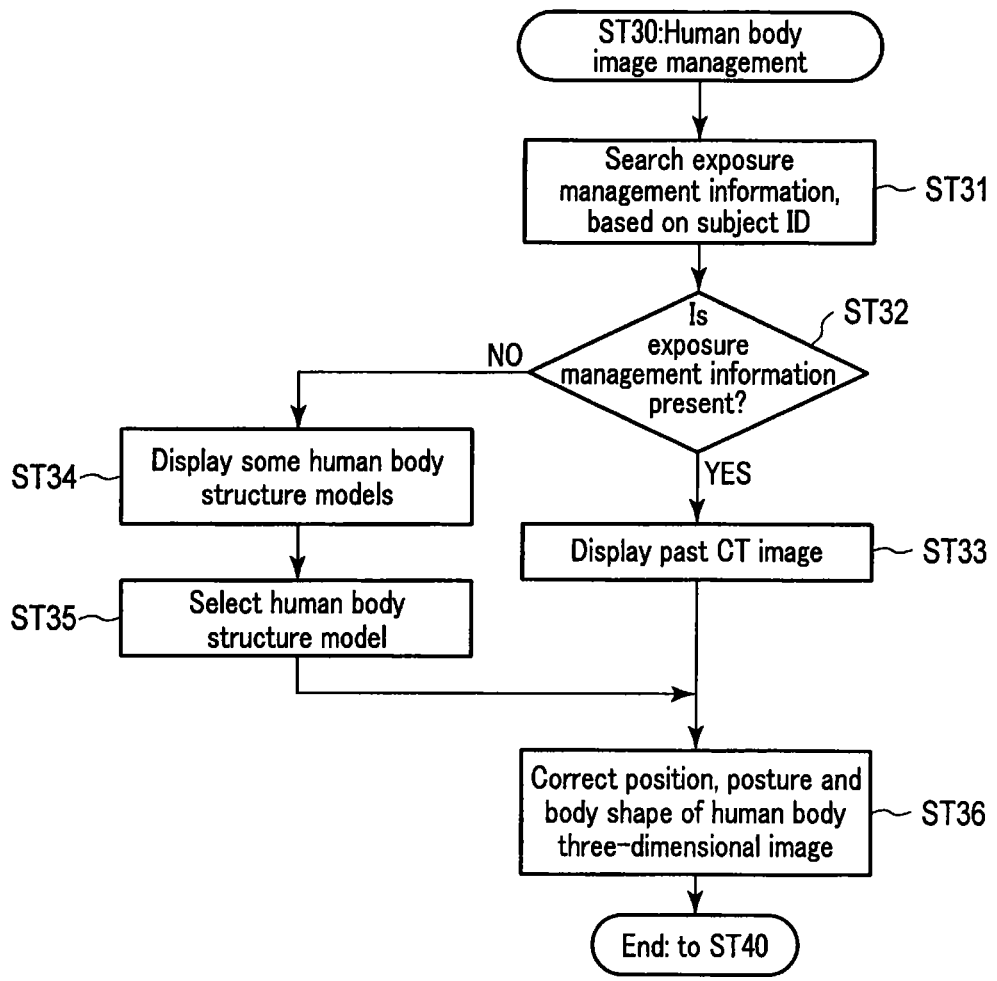
FIG. 5 is a flowchart for describing steps of human body image management in the embodiment.

In step ST30, as illustrated in FIG. 5, the human body image management unit 53 corrects the body shape, position and posture of the human body three-dimensional image so as to agree with the body shape, position and posture of the subject, by utilizing the collected X-ray images and the geometrical information of the corresponding apparatus (the geometrical information of the X-ray optical system and the apparatus-specific information) (ST31 to ST36).

Specifically, based on the subject ID in the X-ray irradiation record, the human body image management unit 53 searches the exposure management information (human body image management information and exposure dose management information) in the management memory 52 (ST31).

If the exposure management information is present (ST32; Y), the human body image management unit 53 displays the past CT image on the display unit 56 as the human body three-dimensional image (ST33).

The human body image management unit 53 compares the CT image photographed in the past with the CT image photographed this time, and corrects the human body three-dimensional image. Specifically, the human body image management unit 53 corrects misalignment between the position of the subject in the X-ray irradiation step and the position of the human body three-dimensional image. For example, when the present medical step is an X-ray examination, the human body image management unit 53 executes projection in accordance with the geometrical information of the X-ray optical system, and corrects the position and posture of the human body three-dimensional image so as to match with the corresponding X-ray image (ST36). In this manner, the human body image management unit 53 locally corrects misalignment each time an X-ray image of the subject is collected, and ends the correction of misalignment if the misalignment decreases to a predetermined amount or less. The same applies to the case of the human body structure model M.

On the other hand, if the exposure management information is not present (ST32; N), the human body image management unit 53 displays on the display unit 56 some human body structure models M in the management memory 52 (ST34), and selects the human body structure models M closest to the body shape of the subject as the human body three-dimensional image (ST35). In this selection, the numerical values of the body shape of the subject (e.g., the body height, head circumference, chest circumference, abdominal circumference, arm circumference, and leg circumference) and the numerical values of the human body structure model M may be compared, or designation of the human body structure model M by the operator may be accepted.

Thereafter, the human body image management unit 53 corrects misalignment between the position of the subject in the X-ray irradiation step and the position of the human body structure model M. In addition, the human body image management unit 53 compares local regions between the X-ray image of the subject in each X-ray irradiation step and the human body structure model M, associates the local regions with each other, and then distorts the human body structure model M, based on the associated result.

Figure 6:
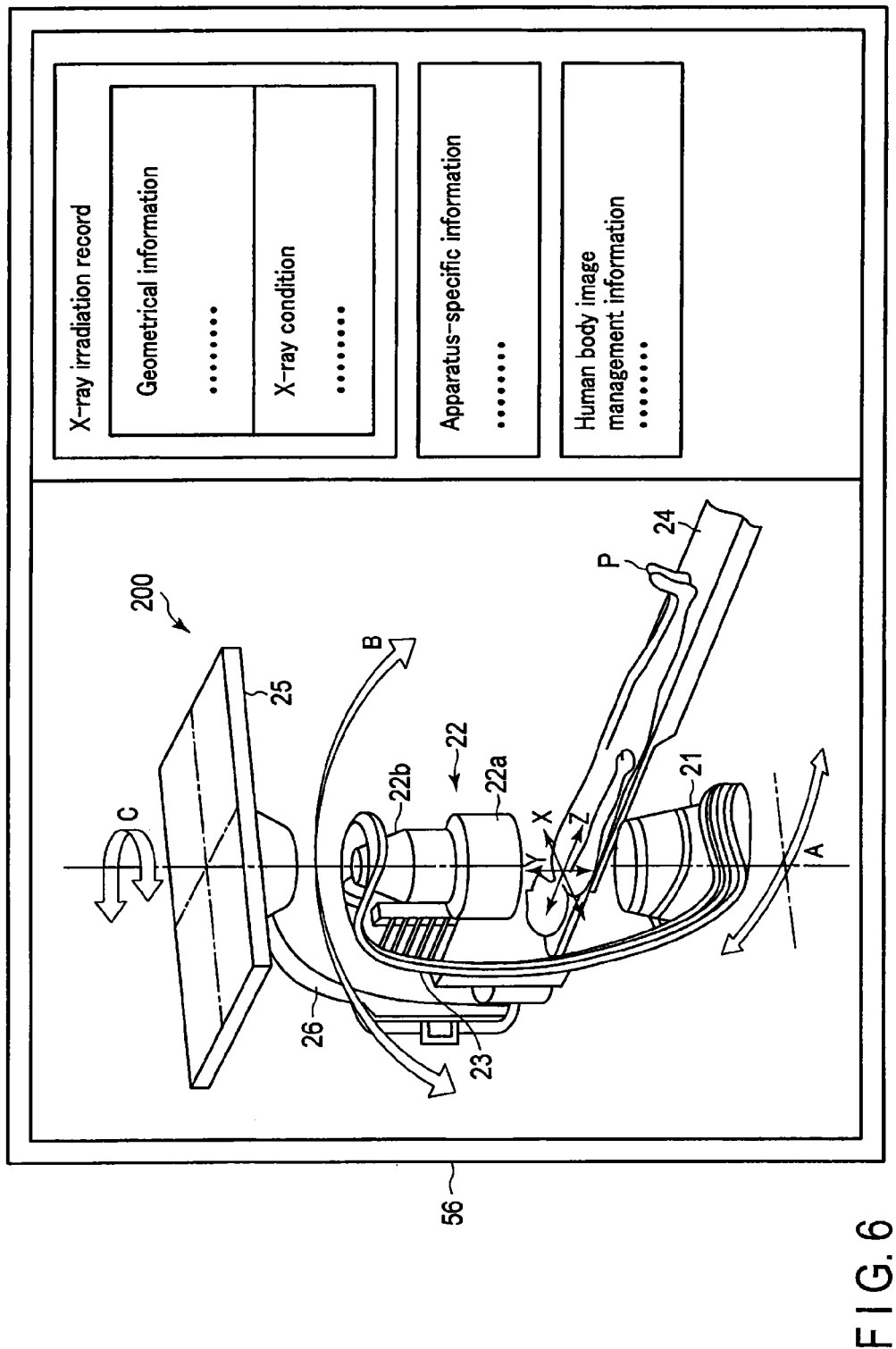
FIG. 6 is a schematic view illustrating a display example of a three-dimensional image after correction in the embodiment.

For example, the human body image management unit 53 projects the selected human body structure model M, like the CT image, in accordance with the geometrical information of the X-ray optical system, and corrects the position, posture and body shape of the human body structure model M so as to match with the corresponding X-ray image (ST36). The human body three-dimensional image after the correction is displayed on the display unit 56, for example, as illustrated in FIG. 6. In addition, the human body image management information relating to the human body three-dimensional image after the correction is written in the management memory 52 by the human body image management unit 53. The human body image management information is information in which the subject ID, the human body three-dimensional image ID, the identification information of the X-ray irradiation step, and the position, posture and body shape of the subject are associated.

After the end of step ST30 which comprises steps ST31 to ST36, the exposure dose management unit 54 executes exposure dose management (ST40).

In step ST40, the position, posture and body shape of the subject have already been identified. Thus, as illustrated in FIG. 7, the exposure dose management unit 54 identifies the skin exposure dose and skin exposure area on the surface of the subject, based on the X-ray irradiation record including the geometrical information of the X-ray optical system and the X-ray conditions (including the irradiation time) (ST41). Incidentally, if the position, posture and body shape of the subject are locally corrected, the skin exposure dose and skin exposure area are recalculated based on the corrected amount.

The exposure dose management unit 54 adds the identified skin exposure dose and skin exposure area to the human body three-dimensional image (ST42).

The exposure dose management unit 54 records the added result onto the human body three-dimensional image in each X-ray irradiation step (ST43). For example, exposure doses involved in a CT examination of the first day, an X-ray angiography examination of the second day and a medical treatment by the X-ray angiography apparatus 20 of the third day are recorded on the human body three-dimensional image as separate data. Specifically, the exposure dose management unit 54 writes the exposure dose management information in the management memory 52 in each X-ray irradiation step. Incidentally, the exposure amount management information is information in which the subject ID, the human body three-dimensional image ID, the identification information of the X-ray irradiation step, the date/time information indicative of the date/time of the irradiation step, the skin exposure dose and the skin exposure area are associated.

After the end of step ST40 comprising steps ST41 to ST43, the exposure dose management unit 54 executes display (ST50).

Figure 8:
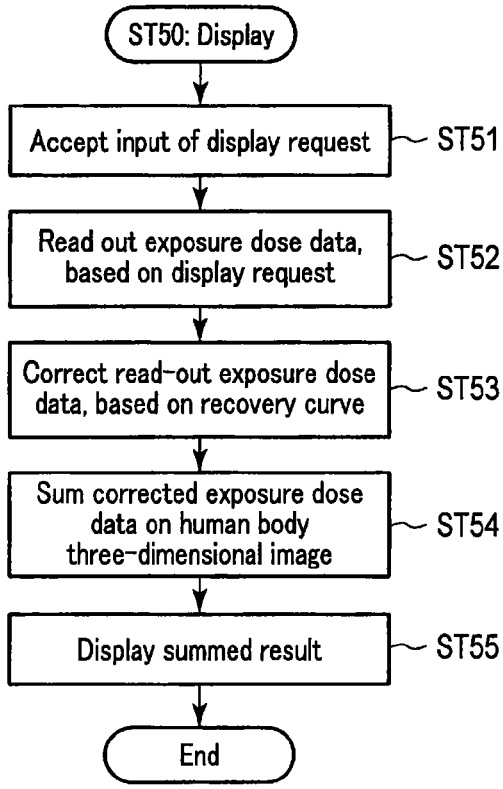
FIG. 8 is a flowchart for describing steps of display in the embodiment.

In step ST50, as illustrated in FIG. 8, upon accepting an input of a display request designating identification information or time range information indicative of a time range including the date/time (ST51), the exposure dose management unit 54 reads out the skin exposure dose, skin exposure area and date/time information from the management memory 52, based on the designated identification information or time range information (ST52). For example, upon accepting a display request designating time range information of the past week, the exposure dose management unit 54 reads out the skin exposure dose, skin exposure area and date/time information of the past week from the management memory 52.

The exposure dose management unit 54 calculates the sum of each of the non-recovered skin exposure dose and skin exposure area, based on the read-out skin exposure dose and skin exposure area and the recovery degree which is determined (on a recovery curve) by the elapsed time from the date/time indicated by the read-out date/time information (ST53, ST54). For example, in the case of 95% recovery from the X-ray exposure of one week ago, only 5% is added to the exposure dose on the human body three-dimensional image. Incidentally, the value of the recovery degree may vary from region to region. Specifically, the exposure dose management unit 54 may include recovery curves varying from region to region.

In addition, when the correction based on the recovery curve in step ST53 is not executed, the exposure dose management unit 54 reads out the skin exposure dose and skin exposure area (the exposure dose management unit 54 does not read out the date/time information) in step ST52, based on the identification information or time range information in the display request, and calculates the sum of each of the skin exposure dose and skin exposure area in step ST53.

Figure 9:
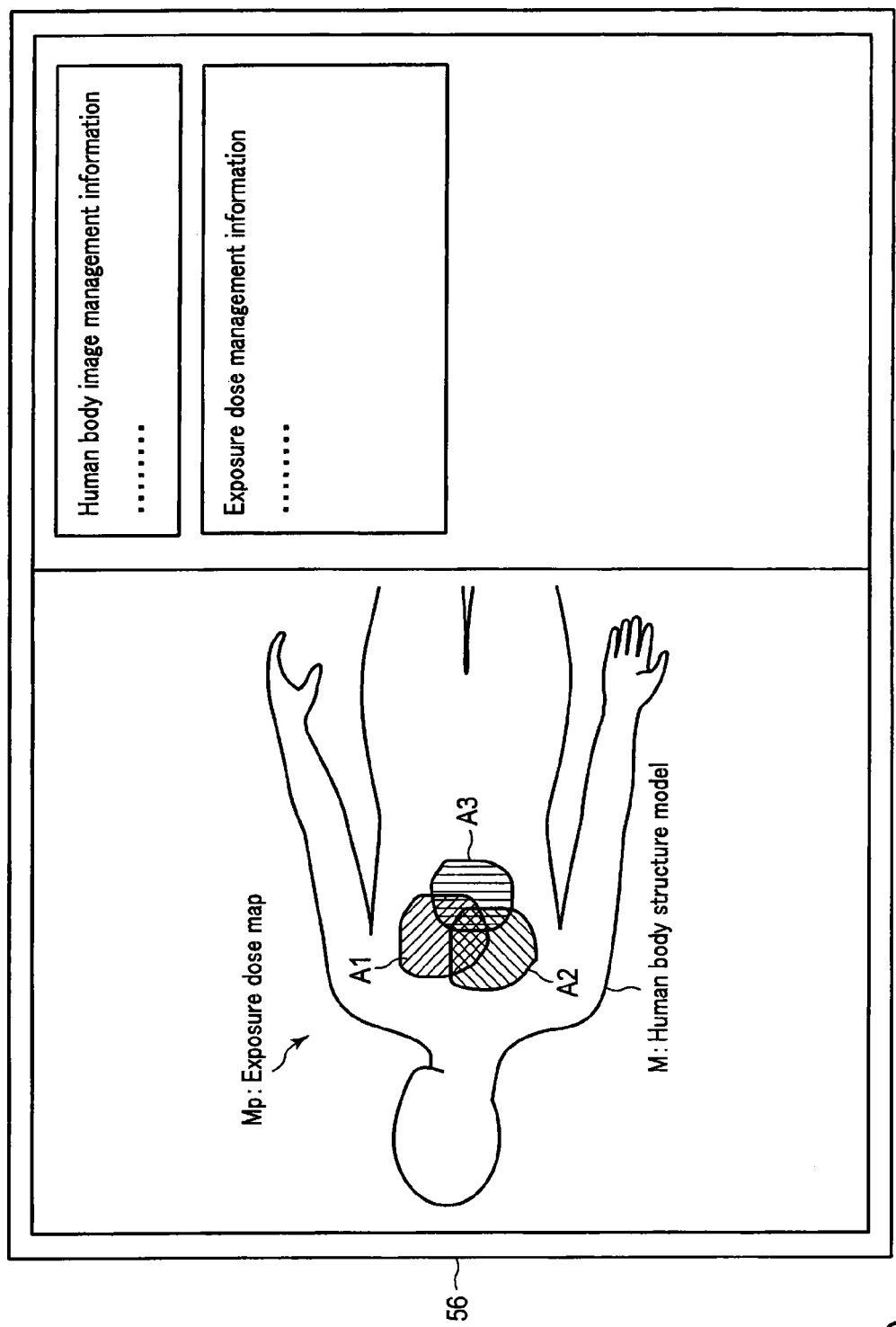
FIG. 9 is a schematic view illustrating a display example of an exposure dose map in the embodiment.

In any case, the exposure dose management unit 54 displays the calculated skin exposure dose and skin exposure area on the human body three-dimensional image (ST55). At this time, for example, as illustrated in FIG. 9, the display unit 56 displays an exposure dose map Mp in which skin exposure doses and skin exposure areas A1 to A3 are recorded on the human body structure model M. This display is similar in the case of the human body three-dimensional image based on the CT image.

By the above, the management of the exposure dose, which is involved in the examination/medical treatment this time, is terminated.

At a later date, if the next examination/medical treatment is performed and the examination/medical treatment is completed (ST10), steps ST20 to ST50 are executed in the same manner as described above. In addition, the exposure dose management unit 54 updates the skin exposure dose after the passing of a predetermined period to a zero value, based on the skin exposure dose and date/time information in the management memory 52.

As has been described above, according to the present embodiment, the exposure dose and exposure area of the subject in the first irradiation step are recorded on the human body three-dimensional image, misalignment between the position of the subject in the second irradiation step and the position of the human body three-dimensional image is corrected, and the exposure dose and exposure area in the second irradiation step are further recorded on the human body three-dimensional image in which the misalignment was corrected. By this configuration, the exposure dose, which is accumulated by a plurality of times of irradiation, can be managed.

Additionally, according to the embodiment, based on the human body three-dimensional image, the exposure dose management information of a plurality of examinations is integrated. By this configuration, the risk of radiation exposure damage in the entirety of the diagnosis and medical treatment can always be understood.

Additionally, in step ST50, when a result in which recovery is taken into account is displayed by using the result of the recovery curve, the risk due to radiation exposure can more exactly be understood.

Additionally, in the embodiment, only the skin exposure dose is calculated. However, the exposure dose of internal organs with high sensitivity to exposure, such as the eye and thyroid gland, may be managed. In this case, the intensity of X rays reaching the internal organ is calculated by using a radiation absorption coefficient distribution of a human body three-dimensional image, and the exposure of the internal organ is calculated based on this intensity.

SECOND EMBODIMENT

Next, an exposure dose management system according to a second embodiment is described with reference to the above-described FIG. 1.

Figure 10:
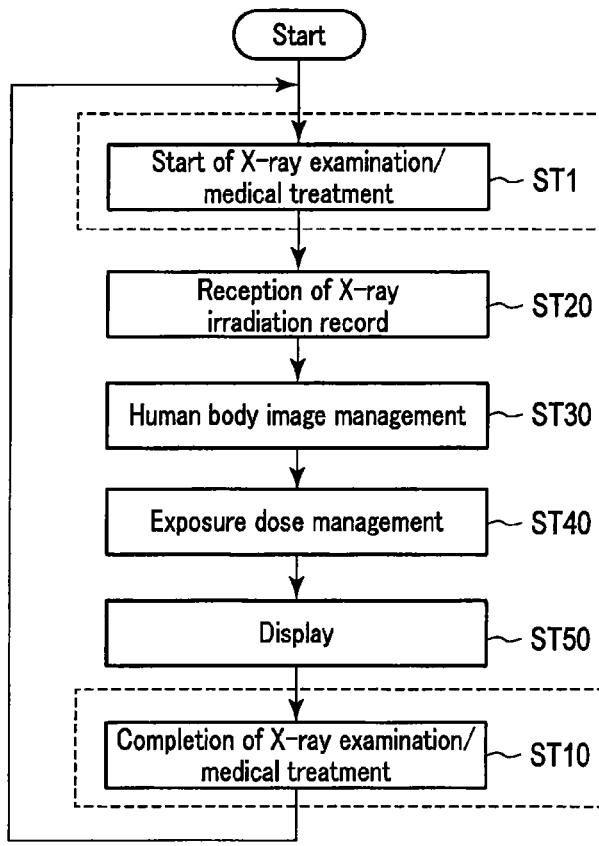
FIG. 10 is a flowchart for describing an operation of an exposure dose management system according to a second embodiment.

The second embodiment is a modification of the first embodiment. Unlike the first embodiment in which the exposure dose map Mp is updated after the end of the examination, the second embodiment is configured to successively update the exposure dose map Mp during the examination, as illustrated in FIG. 10. Incidentally, FIG. 10 illustrates that the above-described steps ST20 to ST50 are executed between step ST1, which indicates the start of the X-ray examination/medical treatment, and step ST10 which indicates the end of the X-ray examination/medical treatment.

In the second embodiment, when the human body image management cannot be determined at the initial stage of the X-ray examination, the human body image management is executed once again each time a new image is collected, and the precision is gradually updated. In this case, at each time of update, the exposure dose management from the beginning is executed once again. For example, a standard human body three-dimensional image is assumed at the beginning, and an exposure dose based on the human body three-dimensional image is displayed. Thereafter, each time an X-ray image in a frontal direction or a lateral direction is received, the human body three-dimensional image is recalculated and the precision is gradually enhanced. In addition, each time the human body three-dimensional image is recalculated, the exposure dose and exposure area are recalculated from the beginning.

According to the above-described configuration, in addition to the advantageous effects of the first embodiment, it is possible to more exactly understand the risk of the patient due to exposure, since the risk due to exposure can be understood comprehensively during examinations (including not only a single examination but also previous examinations).

THIRD EMBODIMENT

Figure 11:
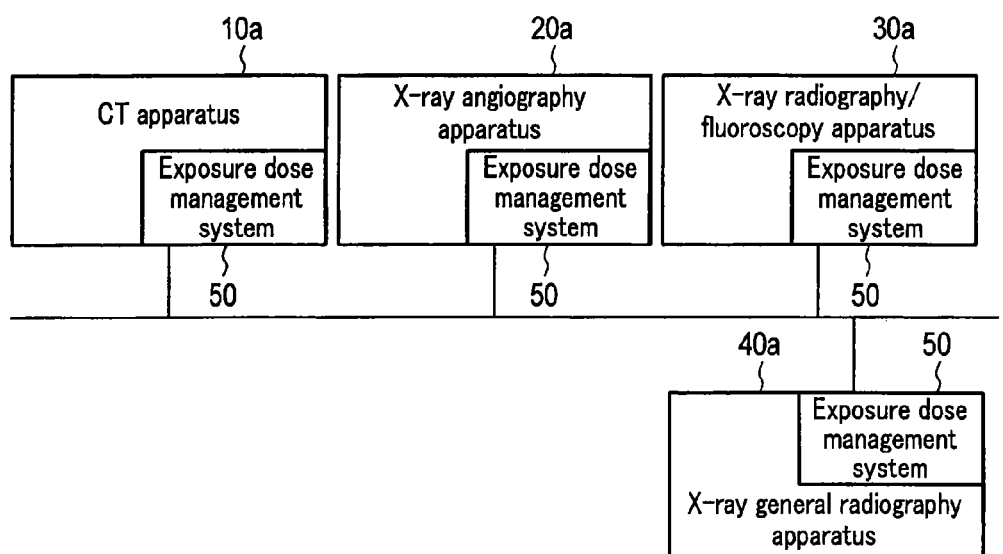
FIG. 11 is a schematic view illustrating an example of an exposure dose management system according to a third embodiment and a peripheral configuration thereof.

FIG. 11 is a schematic view illustrating an example of an exposure dose management system according to a third embodiment and a peripheral configuration thereof. Substantially the same parts as in FIG. 1 are denoted by like reference numerals, and a detailed description thereof is omitted. Different parts will mainly be described. Similarly, an overlapping description will be omitted in connection with the respective embodiments to be described below.

The third embodiment is a modification of the first or second embodiment, and an exposure dose management system 50 is included in each of a CT apparatus 10a, an X-ray angiography apparatus 20a, an X-ray radiography/fluoroscopy apparatus 30a and an X-ray general radiography apparatus 40a.

Figure 12:
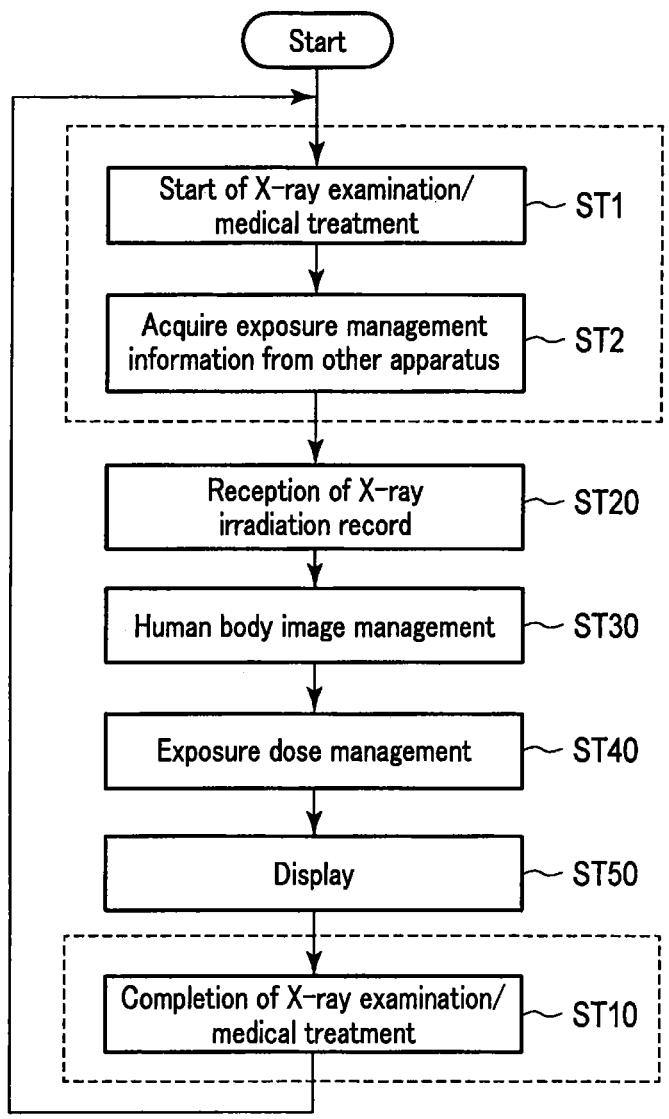
FIG. 12 is a flowchart for describing an operation in the embodiment.

Accordingly, as illustrated in FIG. 12, the exposure dose management system 50 in each apparatus, 10a to 40a, includes, in addition to the above-described functions, a function of sending, based on a subject ID the input of which was accepted, an exposure management information transmission request designating the subject ID to other apparatuses, 10a to 40a, and acquiring all associated exposure management information (human body image management information and exposure dose management information) from the other apparatuses, 10a to 40a, at the time of the start of the examination. In the meantime, the communication function of the exposure management information between the apparatuses 10a to 40a may be implemented based on, for instance, the DICOM (Digital Imaging and Communication in Medicine) standard. In addition, the exposure management information of the apparatuses 10a to 40a may be searched in step ST31 in the same manner as described above.

Even with the above configuration, the same advantageous effects as in the first or second embodiment can be obtained.

FOURTH EMBODIMENT

FIG. 13 is a schematic view illustrating an example of an exposure dose management system according to a fourth embodiment and a peripheral configuration thereof.

The present embodiment is a modification of the first or second embodiment. A CT apparatus 10b, an X-ray angiography apparatus 20b, an X-ray radiography/fluoroscopy apparatus 30b and an X-ray general radiography apparatus 40b include client units 11, 27, 31 and 41, respectively.

Figure 14:
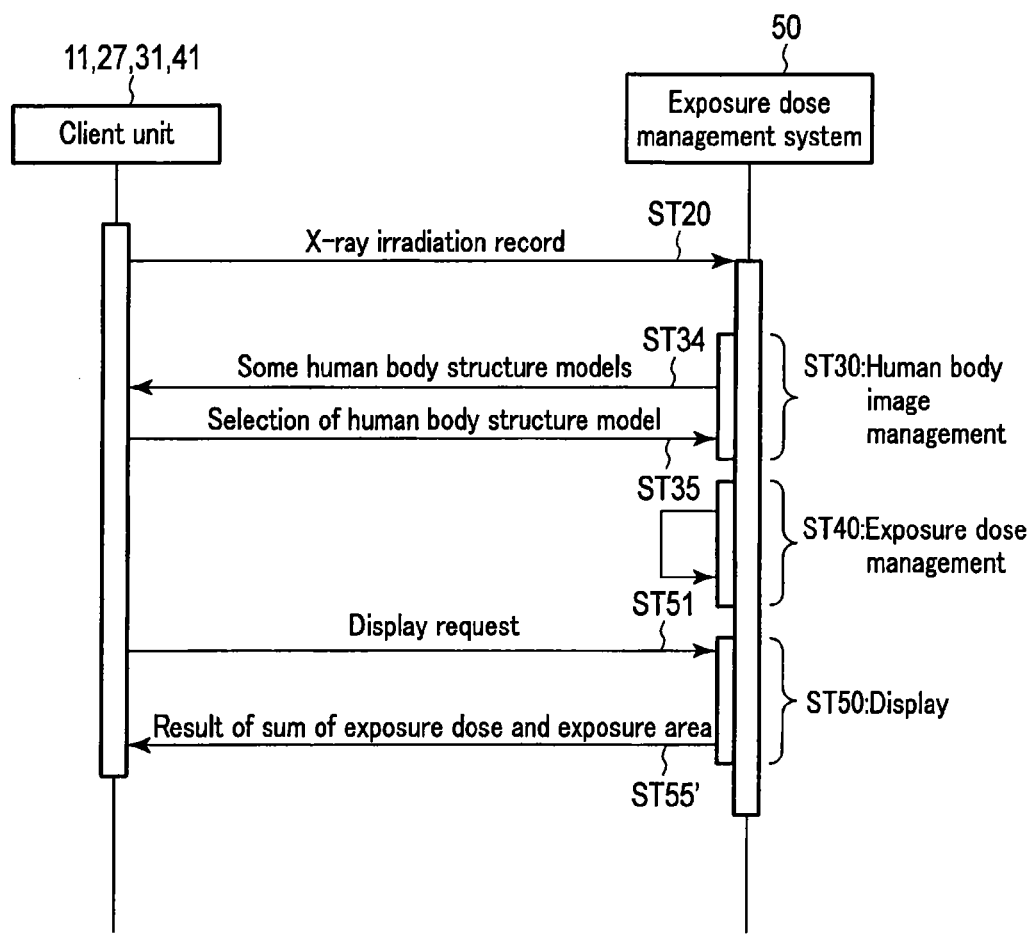
FIG. 14 is a flowchart for describing an operation in the embodiment.

In this case, the client unit 11, 27, 31, 41 is an interface corresponding to an operator's operation, and includes, for example, as illustrated in FIG. 14, a function of communicating with the exposure dose management system 50 in accordance with the operator's operation, and a function of displaying image data which was received from the exposure dose management system 50.

Even with the above configuration, the same advantageous effects as in the first or second embodiment can be obtained.

FIFTH EMBODIMENT

FIG. 15 is a schematic view illustrating an example of an exposure dose management system according to a fifth embodiment and a peripheral configuration thereof.

The present embodiment is a modification of the first and second embodiments. Unlike the first and second embodiments in which the exposure dose of skin exposure by X rays is managed, this embodiment is configured to manage, for example, the exposure dose of internal organ exposure by gamma rays and the exposure dose of exposure by an arbitrary radiation.

Specifically, as illustrated in FIG. 15, in addition to the above-described apparatuses 10 to 40, a PET (positron emission computed tomography) apparatus 60, a SPECT (single photon emission computed tomography) apparatus 70 and a radiotherapy apparatus 80 are connected to the exposure dose management system 50 over the network. Incidentally, the PET apparatus 60 and SPECT apparatus 70 correspond to the configuration for managing the exposure dose of internal organ exposure by gamma rays. The radiotherapy apparatus 80 corresponds to the configuration for managing the exposure dose of exposure by an arbitrary radiation.

In this case, the PET apparatus 60 and SPECT apparatus 70 utilize the property that a radioactive pharmaceutical, which was administered to the subject, accumulates at a specific diseased part. Specifically, the PET apparatus 60 and SPECT apparatus 70 detect gamma rays which are radiated from a nuclear species (RI) included in the radioactive pharmaceutical administered to the subject, and construct an image of density distribution of the RI in the tomographic plane of the subject. Incidentally, in an examination by the PET apparatus 60, a radioactive pharmaceutical including a positron nuclear species is administered to the subject. In an examination by the SPECT apparatus 70, a radioactive pharmaceutical including a single-photon nuclear species is administered to the subject.

For example, in the PET apparatus 60, gamma rays, which are emitted in exactly opposite directions when a positron emitted from a positron nuclear species combines with a nearby negatron and disintegrates, are detected by respective detectors. Thereby, the PET apparatus 60 generates a PET image corresponding to the density distribution in the tomographic plane of the RI existing on a straight line connecting the respective detectors.

Specifically, the PET apparatus 60 is used for an examination including an irradiation step of radiating gamma rays from within the subject, and includes an ordinary PET function. Furthermore, the PET apparatus 60 includes a function of sending, upon completion of the examination, PET images collected by the PET photography and a gamma ray irradiation record, which corresponds to the PET images, to the exposure dose management system 50.

In the SPECT apparatus 70, gamma rays emitted from a single-photon nuclear species are detected by detectors and projection data at respective rotational angles are obtained. Thereby, the SPECT apparatus 70 applies a reconstruction process to these projection data, thus generating a SPECT image corresponding to the density distribution of the RI in the tomographic plane of the subject.

Specifically, the SPECT apparatus 70 is used for an examination including an irradiation step of radiating gamma rays from within the subject, and includes an ordinary SPECT function. Furthermore, the SPECT apparatus 70 includes a function of sending, upon completion of the examination, SPECT images collected by the SPECT photography and a gamma ray irradiation record, which corresponds to the SPECT images, to the exposure dose management system 50.

The distribution in the body of the radioactive pharmaceutical is identified from the obtained PET images or SPECT images. In usual cases, a patient, who undergoes a PET examination or a SPECT examination, underwent an examination by a CT or an MRI beforehand. Thus, by utilizing these images, the distribution in the body of the radiation absorption coefficient is identified and the exposure dose in each internal organ is calculated.

The radiotherapy apparatus 80 is used for a medical treatment including an irradiation step, and includes an ordinary radiographic function. Furthermore, the radiotherapy apparatus 80 includes a function of sending, upon completion of the medical treatment, radiographic images collected by the radiography and an irradiation record, which corresponds to the radiographic images, to the exposure dose management system 50. The radiotherapy apparatus 80 includes a radiation source (not shown) which emits radiation. As the radiation for radiotherapy, for example, use can be made of an arbitrary radiation such as X rays, gamma rays, alpha rays, an electron beam, or a proton beam. In this case, the distribution in the body of the radiation absorption coefficient may be understood by making use of a CT image or an MRI image photographed at a time of a medical treatment plan, and then the exposure dose in each internal organ may be calculated.

According to the above-described configuration, the advantageous effects of the first or second embodiment can be obtained in accordance with the kind of radiation used by respective apparatuses 10 to 80 connected to the network and the contents of the examination and medical treatment. In short, the advantageous effects of the first or second embodiment can be obtained with respect to exposure of an arbitrary region by an arbitrary radiation.

SIXTH EMBODIMENT

FIG. 16 is a schematic view illustrating an example of an exposure dose management system according to a sixth embodiment and a peripheral configuration thereof.

The sixth embodiment is a modification of the third and fifth embodiments and, like the apparatuses 10a to 40a, an exposure dose management system 50 is included in each of a PET apparatus 60a, a SPECT apparatus 70a, and a radiotherapy apparatus 80a.

Accordingly, like the third embodiment, as illustrated in FIG. 12, the exposure dose management system 50 in each apparatus, 10a to 80a, includes a function of sending, based on a subject ID the input of which was accepted, an exposure management information transmission request designating the subject ID to other apparatuses, 10a to 80a, and acquiring all associated exposure management information (human body image management information and exposure dose management information) from the other apparatuses, 10a to 80a, at the time of the start of the examination. In the meantime, the communication function of the exposure management information between the apparatuses 10a to 80a may be implemented based on, for instance, the DICOM standard. In addition, the exposure management information of the apparatuses 10a to 80a may be searched in step ST31 in the same manner as described above.

According to the above-described configuration, the advantageous effects of the third and fifth embodiments can be obtained in accordance with the kind of radiation used by respective apparatus 10a to 80a, which are connected to the network, and the contents of the examination and medical treatment. In short, the advantageous effects of the third and fifth embodiments can be obtained with respect to exposure of an arbitrary region by an arbitrary radiation.

SEVENTH EMBODIMENT

Figure 17:
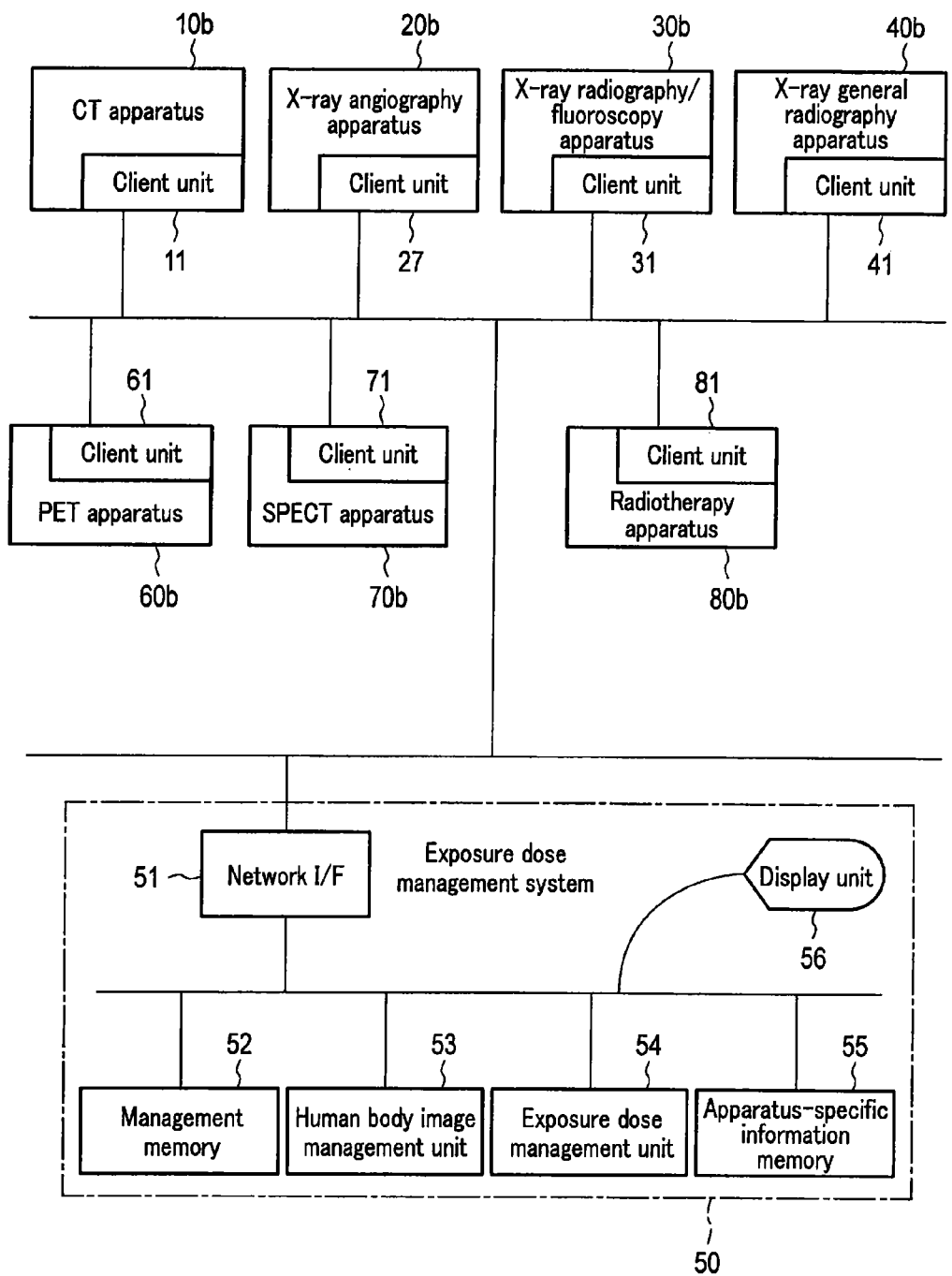
FIG. 17 is a schematic view illustrating an example of an exposure dose management system according to a seventh embodiment and a peripheral configuration thereof.

FIG. 17 is a schematic view illustrating an example of an exposure dose management system according to a seventh embodiment and a peripheral configuration thereof.

The present embodiment is a modification of the fourth and fifth embodiments. Like the apparatuses 10b to 40b, a PET apparatus 60b, a SPECT apparatus 70b and a radiotherapy apparatus 80b include client units 61, 71 and 81, respectively.

In this case, like the fourth embodiment, the client unit 61, 71, 81 is an interface corresponding to an operator's operation, and includes, for example, as illustrated in FIG. 14, a function of communicating with the exposure dose management system 50 in accordance with the operator's operation, and a function of displaying image data which was received from the exposure dose management system 50.

According to the above-described configuration, the advantageous effects of the fourth and fifth embodiments can be obtained in accordance with the kind of radiation used by respective apparatus 10b to 80b, which are connected to the network, and the contents of the examination and medical treatment. In short, the advantageous effects of the fourth and fifth embodiments can be obtained with respect to exposure of an arbitrary region by an arbitrary radiation.

According to at least one of the above-described embodiments, the exposure dose and exposure area of the subject in the first irradiation step are recorded on the human body three-dimensional image, misalignment between the position of the subject in the second irradiation step and the position of the human body three-dimensional image is corrected, and the exposure dose and exposure area in the second irradiation step are further recorded on the human body three-dimensional image in which the misalignment was corrected. By this configuration, the exposure dose, which is accumulated by a plurality of times of irradiation, can be managed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An exposure dose management system, comprising:
a non-transitory memory storing a human body three-dimensional image; and
processing circuitry configured to
record an exposure dose and an exposure area of a subject in a first irradiation step, on the human body three-dimensional image;
correct misalignment between a position of the subject in a second irradiation step, which follows the first irradiation step, and a position of the human body three-dimensional image; and
further record an exposure dose and an exposure area in the second irradiation step, on the human body three-dimensional image in which the misalignment was corrected.

2. The exposure dose management system of claim 1, wherein the human body three-dimensional image is either a CT image of the subject or a human body structure model which is expressed by a radiation absorption coefficient.

3. The exposure dose management system of claim 2, wherein the processing circuitry is further configured to:
compare, when the human body three-dimensional image is the human body structure model, local regions between a radiation image of the subject in each of the irradiation steps and the human body structure model, and associate the local regions with each other; and
distort the human body structure model, based on a result of the association.

4. The exposure dose management system of claim 1, wherein the processing circuitry is further configured to locally correct the misalignment each time a radiation image of the subject is collected.

5. The exposure dose management system of claim 4, wherein the processing circuitry is further configured to recalculate the exposure dose and exposure area, based on the corrected amount.

6. The exposure dose management system of claim 4, wherein the processing circuitry is further configured to end the correction when the misalignment decreases to a predetermined amount or less.

7. The exposure dose management system of claim 1, further comprising an exposure dose display,
wherein the memory stores the recorded exposure dose and the exposure area in association with identification information indicative of the irradiation step or time range information indicative of a date/time of the irradiation step,
the processing circuitry is further configured to read out, upon accepting an input of a display request designating the identification information or the time range information indicative of a time range including the date/time, the exposure dose and the exposure area from the memory, based on the designated identification information or time range information, and
the exposure dose display displays a sum of the read-out exposure dose and the exposure area on the human body three-dimensional image.

8. The exposure dose management system of claim 1, further comprising an exposure dose display,
wherein the memory stores the recorded exposure dose and the exposure area in association with identification information indicative of the irradiation step or time range information indicative of a date/time of the irradiation step,
the processing circuitry is further configured to
read out, upon accepting an input of a display request designating the identification information or the time range information indicative of a time range including the date/time, the exposure dose, the exposure area, and the date/time information from the memory, based on the designated identification information or time range information, and
calculate a sum of each of a non-recovered exposure dose and an exposure area, based on the read-out exposure dose and exposure area and a recovery degree, which is determined by an elapsed time from the date/time indicated by the read-out date/time information, and
the exposure dose display displays the calculated exposure dose and the exposure area on the human body three-dimensional image.

9. The exposure dose management system of claim 8, wherein the recovery degree varies from region to region.

10. The exposure dose management system of claim 8, wherein the processing circuitry is further configured to update, based on the exposure dose and date/time information in the memory, the exposure dose to a zero value, when a predetermined period has passed since the date/time indicated by the date/time information.

11. The exposure dose management system of claim 1, wherein, as the human body three-dimensional image, a human body three-dimensional image which was previously created is reused.

12. The exposure dose management system of claim 1, wherein the exposure dose includes a skin exposure dose or an internal organ exposure dose.

13. An exposure dose management method which is executed by an exposure dose management system including a non-transitory memory that stores a human body three-dimensional image, the method comprising:
recording an exposure dose and an exposure area of a subject in a first irradiation step on the human body three-dimensional image;
correcting misalignment between a position of the subject in a second irradiation step, which follows the first irradiation step, and a position of the human body three-dimensional image; and further recording an exposure dose and an exposure area in the second irradiation step on the human body three-dimensional image in which the misalignment was corrected.

* * * * *